United States Patent [19]

Camenzind et al.

[11] Patent Number: 5,320,764

[45] Date of Patent: Jun. 14, 1994

[54] MULTIFUNCTIONAL LUBRICANT ADDITIVES

[75] Inventors: Hugo Camenzind, Bern, Switzerland; Kay S. Gröninger, Bad Bellingen, Fed. Rep. of Germany; Miles Hutchings, Basel, Switzerland

[73] Assignee: Ciba-Geigy Corporation, Ardsley, N.Y.

[21] Appl. No.: 914,165

[22] Filed: Jul. 14, 1992

[30] Foreign Application Priority Data

Jul. 17, 1991 [CH] Switzerland ............... 2121/91-3

[51] Int. Cl.$^5$ .................... C10M 137/10; C07F 9/17
[52] U.S. Cl. .................... 252/32.7 E; 252/327 R; 252/46.4; 252/46.6; 252/46.7; 252/389.21; 252/400.21; 558/180
[58] Field of Search ............ 558/180; 252/32.7 E, 252/32.7 R, 46.6, 46.7, 46.4, 400.21, 389.21

[56] References Cited

U.S. PATENT DOCUMENTS

| | | | |
|---|---|---|---|
| 2,836,564 | 5/1958 | Roberts et al. | 252/47.5 |
| 3,591,475 | 7/1971 | Greisbaum et al. | 204/158 |
| 4,376,054 | 3/1983 | Zinke . | |
| 4,544,492 | 10/1985 | Zinke et al. . | |
| 4,834,893 | 5/1989 | Doner et al. | 252/32.7 E |
| 4,931,576 | 6/1990 | Wirth et al. . | |
| 5,019,282 | 5/1991 | Farng et al. | 252/32.7 E |

FOREIGN PATENT DOCUMENTS

| | | |
|---|---|---|
| 0125209 | 11/1984 | European Pat. Off. . |
| 0166696 | 1/1986 | European Pat. Off. . |
| 0223916 | 6/1987 | European Pat. Off. . |
| 0398843 | 11/1990 | European Pat. Off. . |
| 0291236 | 1/1991 | European Pat. Off. . |
| 3025277 | 10/1989 | Fed. Rep. of Germany . |

OTHER PUBLICATIONS

Grant and Hackh's Chemical Dictionary, 5th Edition, McGraw-Hill, Inc, (1987) pp. 24 and 587.
Encyclopedia of Polymer Science and Technology, vol. 1, pp. 117-118 (Date Unknown).
WPI Acc No.: 86-008856/02, 1986.
WPI Acc. No.: 81-02350d/03, 1981.
WPI Acc No.: 84-283891/46, 1984.

*Primary Examiner*—Prince Willis, Jr.
*Assistant Examiner*—Alan D. Diamond
*Attorney, Agent, or Firm*—William A. Teoli, Jr.

[57] ABSTRACT

Novel compounds of the formula (I)

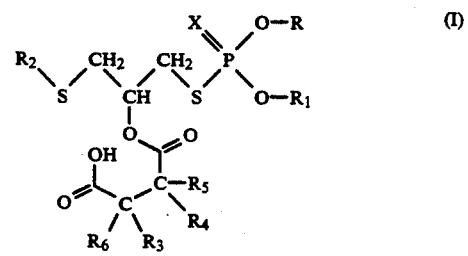

in which X is oxygen or sulfur, R and $R_1$ independently of one another are $C_3$-$C_{30}$alkyl, $R_2$ is $C_4$-$C_{18}$alkyl and $R_3$, $R_4$, $R_5$ and $R_6$ independently of one another are H, $C_1$-$C_{20}$alkyl, $C_3$-$C_{20}$alkenyl, benzyl, phenyl or phenyl which is substituted by $C_1$-$C_{12}$alkyl, and in which $R_5$ and $R_6$ can also be a direct bond, or $R_3$ and $R_4$ together are trimethylene, tetramethylene,

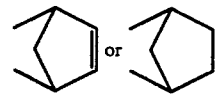

and $R_5$ and $R_6$ are a direct bond or H, or in each case $R_3$ and $R_6$ together are a group $=CH_2$ and $R_4$ and $R_5$ are H, or $R_4$ and $R_5$ together are a group $=CH_2$ and $R_3$ and $R_6$ are H, or $R_3$, $R_4$, $R_5$ and $R_6$ together are

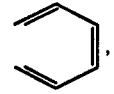

and salts of these compounds, are described. They can be employed as multipurpose additives, in particular as anticorrosion, high pressure and antiwear additives, and as antioxidants in the lubricants and hydraulic or metalworking fluids.

13 Claims, No Drawings

MULTIFUNCTIONAL LUBRICANT ADDITIVES

The invention relates to novel reaction products of S-(2-hydroxy-3-S-alkyl)-propyl O,O-dialkyl esters of mono- or dithiophosphoric acid with cyclic anhydrides, their use as multipurpose additives, in particular as anticorrosion, high pressure and antiwear additives and antioxidants, in lubricants and hydraulic or metalworking fluids, and to compositions comprising at least one of these compounds.

During typical use, lubricants and hydraulic and metalworking fluids in permanent contact with the surface of metallic materials are exposed to high temperatures and the influence of atmospheric oxygen and moisture. More prolonged use therefore leads to oxidative degradation, which can be accelerated catalytically by the contact with metal. This often leads to an increase in the acidity and viscosity of the liquid, so that corrosion of the surface of the material is promoted and the general use properties deteriorate.

It is known for additives to be added to the oils used in lubricating systems. Those which are of great importance are, for example, additives which suppress oxidative degradation of the lubricants, those which protect the moving metal components from wear, additives which have a protective action against high pressure and those which act as anticorrosion or rustproofing agents. However, in many cases, the various types of additives impede one another in their action; thus, for example, many corrosion inhibitors reduce the action of the high pressure additives.

This antagonism can be overcome by using a multifunctional additive. Some classes of compounds which are capable of achieving several of the desired actions have already been described; for example, EP-A 398 843 describes triazine compounds which exhibit both a corrosion-inhibiting and a wear-inhibiting action;

U.S. Pat. No. 2,836,564 describes novel reaction products of alpha-halogenated aliphatic monocarboxylic acids and 2,5-dimercapto-1,3,4-thiadiazole and their use as anticorrosion and rustproofing agents; the usability of the reaction products of alpha-halogenated half-esters or amides of pyruvic acid and thiazole dimercaptides as multifunctional additives with a protective action against high pressure, wear, oxidation and corrosion is mentioned in EP-A 223 916;

the usability of carboxylic acid derivatives bonded to an aliphatic radical via a disulfide bridge in the alpha-position as additives having an anticorrosion and antiwear function is mentioned in EP-A 291 236;

EP-A 166 696 proposes, inter alia, alkyl-thiaglycidyl thiophosphates as additives to lubricants having an oxidation- and corrosion-preventing action and for improving the high pressure and antiwear properties;

U.S. Pat. No. 4,834,893 discloses the usability, inter alia, of some anhydride half-esters which are derived from dithiophosphates, such as mono[(O,O-di-2-ethylhexyl-S-2-hydroxypropyl)phosphorodithioate]-dodecenylsuccinic acid ester and metal salts thereof, in particular the Li and Cu salt, as additives to lubricants and liquid fuels. The compounds have an action as antioxidants and as antiwear and rustproofing agents, as well as a potential action as corrosion inhibitors. Esters, amides and amine salts of such compounds are described in U.S. Pat. No. 5,019,282.

The invention relates to novel compounds which have several of the abovementioned properties, which renders them particularly suitable multipurpose additives. In addition to having an action as antiwear and anticorrosion agents and an antioxidant action, the compounds also have properties which render them usable as additives in high pressure protection. The integration of wear protection, corrosion protection and high pressure protection in one additive is particularly surprising.

The invention relates to compounds of the formula (I)

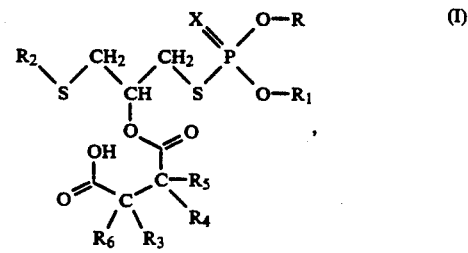

in which X is oxygen or sulfur, R and $R_1$ independently of one another are $C_3$–$C_{30}$alkyl, $R_2$ is $C_4$–$C_{18}$alkyl and $R_3$, $R_4$, $R_5$ and $R_6$ independently of one another are H, $C_1$–$C_{20}$alkyl, $C_3$–$C_{20}$alkenyl, benzyl, phenyl or phenyl which is substituted by $C_1$–$C_{12}$alkyl, and in which $R_5$ and $R_6$ can also be a direct bond, or $R_3$ and $R_4$ together are trimethylene, tetramethylene,

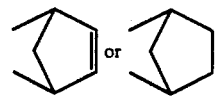

and $R_5$ and $R_6$ are a direct bond or H; or $R_3$ and $R_6$ together are a group =$CH_2$ and $R_4$ and $R_5$ are H; or $R_4$ and $R_5$ together are a group =$CH_2$ and $R_3$ and $R_6$ are H; or $R_3$, $R_4$, $R_5$ and $R_6$ together are

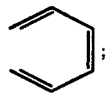

and salts of these compounds.

The numerical range mentioned in the index of the symbol C relates to the number of possible C atoms.

Alkyl radicals R, $R_1$, $R_2$, $R_3$, $R_4$, $R_5$ and $R_6$ in the above formulae are branched or unbranched radicals. Within the above definition as alkyl they are, for example, methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl, pentacosyl or triacontyl.

$C_3$–$C_{20}$Alkenyl radicals $R_3$, $R_4$, $R_5$ and $R_6$ can likewise be branched and unbranched radicals. This meaning includes, inter alia, propenyl, isopropenyl, 2-butenyl, 3-butenyl, isobutenyl, n-penta-2,4-dienyl, 3-methylbut-2-enyl, n-oct-2-enyl, n-dec-2-enyl, n-dodec-2-enyl, iso-dodecenyl, n-octadec-2-enyl and n-octadec-4-enyl.

Phenyl radicals $R_3$, $R_4$, $R_5$ and $R_6$ substituted by $C_1$-$C_{12}$alkyl include, for example, methylphenyl, dimethylphenyl, trimethylphenyl, ethylphenyl, diethylphenyl, isopropylphenyl, tert-butylphenyl, di-tert-butylphenyl, methyl-di-t-butylphenyl, 1,1,3,3-tetramethylbutylphenyl and 1,1,3,3,5,5-hexamethylhexylphenyl. The number of alkyl groups in the alkylphenyl radical is, in particular, 1-3, for example 1 or 2, especially 1.

Preferred compounds of the formula (I) are those in which R and $R_1$ independently of one another are $C_3$-$C_{18}$alkyl, in particular $C_3$-$C_{12}$alkyl, for example propyl, isopropyl, 2-methylpropyl, sec-butyl, n-butyl, n-pentyl, 2-methylbutyl, 3-methylbutyl, n-hexyl, 2-ethylhexyl, n-octyl, isooctyl and n-dodecyl; compounds which are of particular interest are those in which R and $R_1$ are identical and are isopropyl or 2-methylpropyl.

$R_2$ is preferably $C_4$-$C_{12}$alkyl, in particular branched $C_4$-$C_{12}$alkyl, for example tert-butyl, neopentyl, 1-methylheptyl, 1,1,3,3-tetramethylpentyl, tert-nonyl, 1,1,3,3,5,5-hexamethylhexyl or tert-dodecyl, in particular tert-nonyl and tert-dodecyl.

Tert-nonyl (abbreviated to t-nonyl) is to be understood as meaning the isomer mixture comprising 1,1,3,3-tetramethylpentyl, as is defined for tert-nonylmercaptan (Chemical Abstracts Reg. No. 25360-10-5). Correspondingly, tert-dodecyl (abbreviated to t-dodecyl) is to be understood as meaning the isomer mixture comprising 1,1,3,3,5,5-hexamethylhexyl, as is defined for tert-dodecylmercaptan (Chemical Abstracts Reg. No. 25103-58-6).

Compounds which are furthermore preferred are those in which one of the substituents $R_3$ or $R_4$ is H, $C_1$-$C_{20}$alkyl or $C_3$-$C_{20}$alkenyl and the other is hydrogen, or $R_3$ and $R_4$ together are trimethylene, tetramethylene,

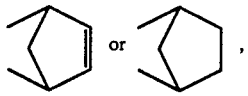

and $R_5$ and $R_6$ are hydrogen or a direct bond, or $R_3$, $R_4$, $R_5$ and $R_6$ together are

Particularly preferred compounds of the formula (I) are those in which one of the substituents $R_3$ or $R_4$ is $C_1$-$C_{20}$alkyl or $C_4$-$C_{20}$alkenyl, for example methyl, ethyl, propyl, n-octyl, isooctyl, n-oct-2-enyl, n-dodecyl, n-dodec-2-enyl, iso-dodecenyl or n-$C_{18}H_{37}$, specifically $C_8$-$C_{12}$alkenyl and $C_8$-$C_{12}$alkyl, in particular n-oct-2-enyl and iso-dodecenyl or iso-dodecyl, and the other is hydrogen, or $R_3$ and $R_4$ together are trimethylene or tetramethylene, in particular tetramethylene.

$R_5$ and $R_6$ are preferably hydrogen or a direct bond, in particular hydrogen.

X is preferably a sulfur atom.

The preferred compounds include compounds of the formula (I) in which R and $R_1$ independently of one another are $C_3$-$C_{18}$alkyl and $R_2$ is $C_4$-$C_{18}$alkyl, one of the substituents $R_3$ or $R_4$ is H, $C_1$-$C_{20}$alkyl or $C_3$-$C_{20}$alkenyl and the other is hydrogen, or $R_3$ and $R_4$ together are trimethylene, tetramethylene,

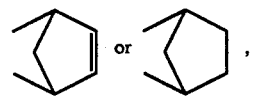

and $R_5$ and $R_6$ are hydrogen or a direct bond, or $R_3$, $R_4$, $R_5$ and $R_6$ together are

Particularly preferred compounds of the formula (I) are those in which X is sulfur, R and $R_1$ independently of one another are $C_3$-$C_{12}$alkyl; $R_2$ is $C_4$-$C_{12}$alkyl; one of the substituents $R_3$ or $R_4$ is $C_1$-$C_{20}$alkyl or $C_4$-$C_{20}$alkenyl and the other is hydrogen; or $R_3$ and $R_4$ together are trimethylene or tetramethylene; and $R_5$ and $R_6$ are hydrogen or a direct bond.

Compounds of the formula (I) which are of particular interest are those in which R and $R_1$ are in each case identical and are isopropyl, 2-methylpropyl, n-butyl, n-pentyl, 2-methylbutyl, 3-methylbutyl or 2-ethylhexyl, $R_2$ is tert-nonyl or -dodecyl, one of the substituents $R_3$ or $R_4$ is oct-2-enyl, $C_{12}$alkenyl or octadecyl and the other is hydrogen, and $R_5$ and $R_6$ are hydrogen.

Compounds of the formula (I) which are especially of interest are those in which R and $R_1$ are in each case identical and are isopropyl or 2-methylpropyl, $R_2$ is tert-nonyl, one of the substituents $R_3$ or $R_4$ is $C_{12}$alkenyl and the other is hydrogen, and $R_5$ and $R_6$ are hydrogen.

Compounds of the formula (I) which are generally of particular interest are those in which R and $R_1$ are identical.

Compounds of the formula (I) which are furthermore preferred are those in which X is sulfur.

This invention also relates to the salts of compounds of the formula (I). These are to be understood as meaning those compounds in which the proton of the free carboxyl group in formula (I) is replaced by one equivalent of a metal cation, for example of an alkali metal or alkaline earth metal or of one of the metals zinc or copper, or by ammonium or ammonium which is mono-, di- or trisubstituted by $C_1$-$C_{18}$alkyl. Mixed salts are also possible.

The alkyl substituents of the ammonium are preferably at least one $C_2$-$C_{18}$alkyl radical and if appropriate other identical or different $C_1$-$C_{18}$alkyl radicals. Particularly preferred substituents of the ammonium are $C_2$-$C_{18}$alkyl, in particular $C_8$-$C_{18}$alkyl, and of these in particular $C_8$alkyl, $C_{13}$alkyl and $C_{18}$alkyl.

Preferred metal salts of the compounds according to formula (I) are the lithium, sodium, potassium, magnesium, calcium and copper(II) salts, and the lithium, magnesium and copper(II) salts are particularly preferred.

The alkali metal and the mono- or di-$C_8$-$C_{18}$alkyl-substituted ammonium salts are of particular interest in practice.

The invention furthermore relates to compositions comprising a) a lubricant or a hydraulic or a metal working fluid and b) one or more compounds of the formula (I). Compositions in which component a) is a lubricant are preferred. Preferred forms of component b) are the same as those described above.

The lubricants and hydraulic and metal working fluids which the compositions according to the invention comprise may decompose more or less readily under the influence of heat, electromagnetic radiation, mechanical stress (in particular by shearing forces) and oxidising substances (in particular atmospheric oxygen). Decomposition products formed in this way, like the water present, contribute toward corrosion of the metal surfaces coming into contact with them.

The compounds of the formula (I) serve as protection against such influences and should advantageously be present in the compositions according to the invention to the extent of 0.01 to 10, for example to the extent of 0.01 to 5, preferably to the extent of 0.03 to 3, in particular to the extent of 0.2 to 0.7 (or in combination with other antiwear additives to the extent of 0.03 to 0.25) percent by weight. One or more of these compounds can be present here. The percentage data relate to the total weight of these compounds, and the basis of calculation is the total weight of component a) and any other components, without component b) (compounds of the formula (I)).

The invention furthermore relates to the use of compounds of the formula (I) as multipurpose additives, in particular in lubricants and metal working and hydraulic fluids. Such a use also means a process for improving the use properties of lubricants and metal working and hydraulic fluids. The use according to the invention also includes protection of the metal components to be lubricated from mechanical erosion (wear protection).

The lubricants and metal working and hydraulic fluids in question are based on, for example, mineral or synthetic oils or mixtures thereof. The lubricants are familiar to the expert and are described in the relevant technical literature, for example in Dieter Klamann, "Schmierstoffe und verwandte Produkte (Lubricants and Related Products)" (Verlag Chemie, Weinheim 1982), in Schewe-Kobek, "Das Schmiermittel-Taschenbuch (The Lubricants Pocketbook)" (Dr. Alfred Hüthig-Verlag, Heidelberg 1974) and in "Ullmanns Enzyklopädie der technischen Chemie (Ullmann's Encyclopedia of Industrial Chemistry)", volume 13, pages 85–94 (Verlag Chemie, Weinheim 1977).

The lubricants are, in particular, oils and fats, for example those based on a mineral oil. Oils are preferred.

Another group of lubricants which can be used vegetable or animal oils, fats, tallows and waxes or mixtures thereof with one another or mixtures with the mineral or synthetic oils mentioned. Vegetable or animal oils, fats, tallows and waxes are, for example, palm-kernel oil, palm oil, olive oil, colza oil, rapeseed oil, linseed oil, groundnut oil, soybean oil, cotton oil, sunflower oil, pumpkin seed oil, coconut oil, maize oil, castor oil, walnut oil and mixtures thereof, fish oil, tallows from slaughtered animals, neat's-foot oil and bone oil, as well as modified, epoxidised and sulfoxidised forms thereof, for example epoxidised soybean oil.

The mineral oils are based on, in particular, hydrocarbon compounds.

Examples of synthetic lubricants include lubricants based on aliphatic or aromatic carboxylic esters, on polymeric esters, on polyalkylene oxides, on phosphoric acid esters, on poly-α-olefins or on silicones, or on a diester of a dibasic acid with a monohydric alcohol, for example dioctyl sebacate or dinonyl adipate, on a triester of trimethylolpropane tricaprylate or mixtures thereof, on a tetraester of pentaerythritol with a monobasic acid or a mixture of such acids, for example pentaerythritol tetracaprylate, or on a complex ester of monobasic and dibasic acids with polyhydric alcohols, for example a complex ester of trimethylolpropane with caprylic and sebacic acid, or of a mixture thereof. In addition to mineral oils, particularly suitable lubricants are, for example, poly-α-olefins, lubricants based on esters, phosphates, glycols, polyglycols and polyalkylene glycols, and mixtures thereof with water.

The metal working fluids and hydraulic fluids can be prepared on the basis of the same substances as described above for the lubricants. They are often also emulsions of such substances in water or other liquids.

Lubricant compositions according to the invention are used, for example, in combustion engines, inter alia in motor vehicles.

The compounds according to formula (I) are readily soluble in lubricants and metal working and hydraulic fluids, and are therefore particularly suitable as additives to these substances. Particular reference is made to their surprisingly good wear- and corrosion-inhibiting action.

The invention therefore also relates to a process for improving the use properties of lubricants and metal working and hydraulic fluids, which comprises adding one or more compounds of the formula (I) to these.

The compositions according to the invention can contain several other additives, for example anticorrosion agents, rust inhibitors, metal deactivators, agents for improving the viscosity index, dispersing agents, antioxidants, pour-point depressants or high pressure or antiwear additives, in order to improve their fundamental properties still further. Examples of such coadditives are listed below.

EXAMPLES OF PHENOLIC ANTIOXIDANTS

1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methyl-undec-1'-yl)-phenol, 2,4-dimethyl-6-(1'-methyl-heptadec-1'-yl)-phenol, 2,4-dimethyl-6-(1'-methyl-tridec-1'-yl)-phenol and mixtures thereof.

2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol and 2,6-didodecylthiomethyl-4-nonylphenol.

3. Hydroquinones and alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl stearate and bis-(3,5-di-tert-butyl-4-hydroxyphenyl)adipate.

4. Hydroxylated thiodiphenyl ethers, for example 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol), 4,4'-thio-bis-(3,6-di-sec-amylphenol) and 4,4'-bis-(2,6-dimethyl-4-hydroxyphenyl)disulfide.

5. Alkylidene-bisphenols, for example 2,2'-methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)butane, 2,6-bis-(3-tert-butyl-5-methyl-2-hydroxybenzyl)-4-methylphenol, 1,1,3-tris(5-tert-butyl-4-hydroxy-2-methylphenyl)butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)butyrate], bis-(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane and 1,1,5,5-tetra-(5-tert-butyl-4-hydroxy-2-methylphenyl)pentane.

6. O-, N- and S-Benzyl compounds, for example 3,5,3',5'-tetra-tert-butyl-4,4'-dihydroxydibenzyl ether, octadecyl 4-hydroxy-3,5-dimethylbenzyl-mercaptoacetate, tris-(3,5-di-tert-butyl-4-hydroxybenzyl)-amine, bis-(4-tert-butyl-3-hydroxy-2,6-dimethylbenzyl) dithioterephthalate, bis-(3,5-di-tert-butyl-4-hydroxybenzyl) sulfide and isooctyl 3,5-di-tert-butyl-4-hydroxybenzylmercaptoacetate.

7. Hydroxybenzylated malonates, for example dioctadecyl 2,2-bis-(3,5-di-tert-butyl-2-hydroxybenzyl)malonate, dioctadecyl 2-(3-tert-butyl-4-hydroxy-5-methylbenzyl)malonate, didodecylmercaptoethyl 2,2-bis-(3,5-di-tert-butyl-4-hydroxybenzyl)malonate and di[4-(1,1,3,3-tetramethylbutyl)-phenyl] 2,2-bis-(3,5-di-tert-butyl-4-hydroxybenzyl)malonate.

8. Hydroxybenzyl-aromatics, for example 1,3,5-tris-(3,5-di-tert-butyl-4-hydroxybenzyl)-2,4,6-trimethylbenzene, 1,4-bis-(3,5-di-tert-butyl-4-hydroxybenzyl)-2,3,5,6-tetramethylbenzene and 2,4,6-tris-(3,5-di-tert-butyl-4-hydroxybenzyl)phenol.

9. Triazine compounds, for example 2,4-bis-octylmercapto-6-(3,5-di-tert-butyl-4-hydroxyanilino)-1,3,5-triazine, 2-octylmercapto-4,6-bis-(3,5-di-tert-butyl-4-hydroxyanilino)-1,3,5-triazine, 2-octylmercapto-4,6-bis-(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, 2,4,6-tris-(3,5-di-tert-butyl-4-hydroxyphenylethyl)-1,3,5-triazine, 1,3,5-tris-(3,5-di-tert-butyl-4-hydroxyphenylpropionyl)hexahydro-1,3,5-triazine and 1,3,5-tris-(3,5-dicyclohexyl-4-hydroxybenzyl) isocyanurate.

10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate and the Ca salt of 3,5-di-tert-butyl-4-hydroxybenzyl-phosphonic acid monoethyl ester.

11. Acylaminophenols, for example 4-hydroxylauric acid anilide, 4-hydroxystearic acid anilide and octyl N-(3,5-di-tert-butyl-4-hydroxyphenyl)-carbamate.

12. Esters of β-(3,5-di-tert-butyl-4-hydroxyphenyl)-propionic acid with mono- or polyhydric alcohols, for example with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis-(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo-[2.2.2]-octane.

13. Esters of β-(5-tert-butyl-4-hydroxy-3-methylphenyl)propionic acid with mono- or polyhydric alcohols, for example with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis-(hydroxyethyl)oxalic acid diamide, 3-thiaundecanol, 3-thiapentadecanol, tri-methylhexanediol, trimethylolpropane and 4-hydroxymethyl-1-phospha-2,6,7-trioxabicyclo-[2.2.2]-octane.

14. Esters of β-(3,5-dicyclohexyl-4-hydroxyphenyl)-propionic acid with mono- or polyhydric alcohols, for example with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis-(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo-[2.2.2]-octane.

15. Esters of 3,5-di-tert-butyl-4-hydroxyphenylacetic acid with mono- or polyhydric alcohols, for example with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, tris(hydroxyethyl) isocyanurate, N,N'-bis-(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo-[2.2.2]-octane.

16. Amides of β-(3,5-di-tert-butyl-4-hydroxyphenyl)-propionic acid, for example N,N'-bis-(3,5-di-tert-butyl-4-hydroxyphenylpropionyl)hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)hydrazine.

Examples of aminic antioxidants:
N,N'-di-isopropyl-p-phenylenediamine, N,N'-di-sec-butyl-p-phenylenediamine, N,N'-bis-(1,4-dimethyl-pentyl)-p-phenylenediamine, N,N'-bis-(1-ethyl-3-methylpentyl)-p-phenylenediamine, N,N'-bis-(1-methyl-heptyl)-p-phenylenediamine, N,N'-dicyclohexyl-p-phenylenediamine, N,N'-diphenyl-p-phenylenediamine, N,N'-di-(2-naphthyl-)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluene-sulfonamido)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylamino-phenol, 4-nonanoylamino-phenol, 4-dodecanoylamino-phenol, 4-octadecanoylamino-phenol, di-(4-methoxyphenyl)amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diaminodiphenylmethane, 1,2-di-[(2-methyl-phenyl)-amino]ethane, 1,2-di-(phenylamino)propane, (o-tolyl)biguanide, di-[4-(1',3'-dimethyl-butyl)-phenyl]amine, tert-octylated N-phenyl-1-naphthylamine, a mixture of mono- and dialkylated tert-butyl/tert-octyldiphenylamines, a mixture of mono- and dialkylated isopropyl-/isohexyl mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis-(2,2,6,6-tetramethyl-piperid-4-yl-hexamethylenediamine, bis-(2,2,6,6-tetramethylpiperid-4-yl) sebacate, 2,2,6,6-tetramethylpiperidin-4-one and 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:

a) Benzotriazoles and derivatives thereof, 4- or 5-alkylbenzotriazoles (for example tolutriazole) and derivatives thereof, 4,5,6,7-tetrahydrobenzotriazole and 5,5'-methylenebis-benzotriazole; Mannich bases of benzotriazole or tolutriazole, such as 1-[di(2-ethylhexyl)aminomethyl)tolutriazole and 1-[di(2-ethylhexyl)aminomethyl)benzotriazole; and alkoxyalkylbenzotriazoles, such as 1-(nonyloxymethyl)benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2,4-triazoles, such as 1-[di(2-ethylhexyl)aminomethyl-1,2,4-triazole; alkoxyalkyl-1,2,4-triazoles, such as 1-(1-butoxyethyl)-1,2,4-triazole; and acylated 3-amino-1,2,4-triazoles.

c) Imidazole derivatives, for example 4,4'-methylenebis(2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole, 2,5-dimercaptobenzothiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenyl-succinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids, such as dodecycloxyacetic acid, dodecyloxy(ethoxy)-acetic acid and amine salts thereof, and furthermore N-oleoylsarcosine, sorbitan monooleate, lead naphthenate, alkenylsuccinic acid anhydrides, for example dodecenyl-succinic anhydride, 2-O-(carboxymethyl)-1-O-dodecyl-3-O-methylglycerol and 2-O-(carboxymethyl)-1-O-tetradecyl-3-O-methylglycerol and salts thereof, in particular Na and triethanolamine salts.

b) Nitrogen-containing compounds, for example:

I. Primary, secondary or tertiary aliphatic or cycloaliphatic amines and amine salts of organic and inorganic acids, for example oil-soluble alkylammonium carboxylates, and furthermore 1-[N,N-bis-(2-hydroxyethyl)amino]-3-(4-nonylphenoxy)propan-2-ol.

II. Heterocyclic compounds, for example:

substituted imidazolines and oxazolines, and 2-heptadecenyl-1-(2-hydroxyethyl)imidazoline.

c) Phosphorus-containing compounds, for example:

Amine salts of phosphoric acid partial esters or phosphonic acid partial esters, and zinc dialkyl-dithiophosphates.

d) Sulfur-containing compounds, for example:

Barium dinonylnaphthalene-sulfonates, calcium petroleum-sulfonates, alkylthio-substituted aliphatic carboxylic acids, esters of aliphatic 2-sulfocarboxylic acids and salts thereof.

e) Glycerol derivatives, for example:

Glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of agents which improve the viscosity index are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:

Polymethacrylate and alkylated naphthalene derivatives.

Examples of dispersing agents/surfactants are:

Polybutenylsuccinic acid amides or imides, polybutenylphosphonic acid derivatives and basic magnesium, calcium and barium sulfonates and phenolates.

Examples of antiwear additives are:

Compounds comprising sulfur and/or phosphorus and/or halogen, such as sulfurised olefins and vegetable oils, zinc dialkyl-dithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, di(2-ethylhexyl)aminomethyltolyltriazole, derivatives of 2,5-dimercapto-1,3,4-thiadiazole, ethyl 3-[(bis-isopropyloxy-phosphinothioyl)thio]propionate, triphenyl thiophosphate (triphenylphosphorothioate), tris(alkylphenyl) phosphorothioate and mixtures thereof (for example tris(isononylphenyl) phosphorothioate), diphenyl mononoynlphenyl phosphorothioate, isobutylphenyl diphenyl phosphorothionate, the dodecylamine salt of 3-hydroxy-1,3-thiaphosphetane 3-oxide, trithiophosphoric acid 5,5,5-tris[isooctyl 2-acetate], derivatives of 2-mercaptobenzothiazole, such as 1-[N,N-bis(2-ethylhexyl)aminomethyl]-2-mercapto-1H-1,3-benzothiazole, and ethoxycarbonyl-5-octyl dithiocarbamate.

PREPARATION OF THE COMPOUNDS OF THE FORMULA (I)

The compounds of the formula (I) can be prepared by methods which are known per se, for example by reaction of compounds of the formula (II)

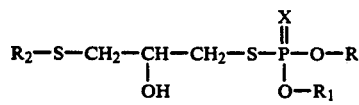

(II)

with corresponding cyclic anhydrides of the formula (III)

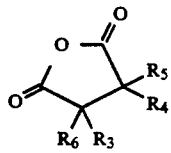

(III)

Compounds of the formula (III) are commercially obtainable in some cases, and can be synthesised by known methods, which are described, for example in: Encyclopedia of Polymer Science and Technology, Volume 1, pages 117 and 118, Interscience Publishers/Wiley, New York 1964. X, R, $R_1$, $R_2$, $R_3$, $R_4$, $R_5$ and $R_6$ in each case are as defined above.

The compounds of the formula (II) known from EP-A 166 696 can be obtained by reaction of a corresponding diester of thiophosphoric acid

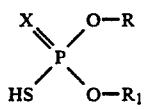

with the desired 2,3-epoxypropyl thioether

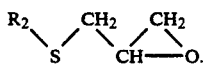

The O,O-diesters of dithiophosphoric acid can be prepared in accordance with U.S. Pat. No. 4,834,893 by reaction of corresponding alcohols with $P_2S_5$. Comparable derivatives of thiophosphoric acid (X=oxygen) can be obtained as ammonium salts and described in EP-A 125 209 by reaction of corresponding phosphites

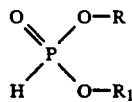

with $S/NH_3$. The ammonium salts can then be further reacted directly with the epoxy compound; see DE-B 3 025 277, or can also first be converted into the corresponding free acid.

For the reaction of the compounds (II) with (III), an approximately equimolar amount of the cyclic anhydride is appropriately added slowly to a chosen amount of the starting compound of the formula (II). The starting compound can be initially introduced into a solvent. Suitable solvents are, for example, toluene or dibutyl ether, or mixtures of the two. The reaction can be carried out in the presence of a catalyst, which is initially introduced together with the starting compound or is added after about half the reaction time. Suitable catalysts are, for example, 4-toluenesulfonic acid, methanesulfonic acid or 4-dimethylamino-pyridine. The mixture is advantageously kept at a constant temperature throughout the entire reaction time. The reaction temperature can be, for example, 20° to 150° C., and is in general 50° to 120° C., preferably 50° to 80° C. The reaction time can be 1 to 24 hours, and is generally between 5 and 16 hours. Working up can be carried out by the methods usually used, for example by washing the organic phase, drying, and removing the solvent.

The isomer mixture ($R_4$ and $R_5$ are not identical to $R_3$ and $R_6$) as a rule obtained (except when symmetric anhydrides are used) can be separated, if desired, with the aid of customary physico-chemical processes. In practice, separation is not necessary. The isomer mixtures can be added as such to the lubricants and metalworking and hydraulic fluids.

To prepare the ammonium salts of compounds of the formula (I), a stoichiometric amount of the corresponding amine, if appropriate also in a solvent, is advantageously added to a solution of the desired compound, and after thorough mixing, the solvent or solvents is or are removed by applying reduced pressure. A suitable solvent is, for example, toluene.

Metal salts of compounds of the formula (I) can be obtained by reaction with corresponding metal hydroxides. The corresponding compound with a free acid function is advantageously introduced into a solvent, the hydroxide is added and the water is then entrained with the solvent by heating the reaction mixture under nitrogen.

To prepare the copper salt, the starting compound is preferably Cu(II) acetylacetonate, which is added to a solution of the compound of the formula (I). After thorough mixing, the acetylacetone liberated and the solvent used are removed in the same manner as in the preparation of the ammonium salts. A suitable solvent is toluene.

A few examples follow for further illustration of the invention. In these examples, and in the rest of the description, parts and percentage data relate to the weight, unless stated otherwise. Iso-dodecenylsuccinic anhydride means the industrial isomer mixture with various $C_{12}H_{23}$ isomers as substituents of succinic anhydride, described under CARN 25377-73-5 as 2,5-furandiones, dihydro-3-(tetrapropenyl). Di-iso-tridecylamine is an industrial product (as defined under CARN 101012-97-9) with two $C_{13}H_{27}$alkyl substituents on the nitrogen atom.

EXAMPLE 1

28.6 g of tert-nonyl (2,3-epoxypropyl) thioether are added dropwise to 27.0 g of O,O'-diisopropyldithiophosphoric acid, while stirring and while cooling with a waterbath at 20°-25° C. After the end of evolution of heat, the mixture is heated at 50° C. for 1 hour. Volatile constituents are then stripped off at 25° C. under 0.2 mbar. 54.1 g (99.8% of theory) of an intermediate remain as a colourless liquid having a refractive index $n_D^{20}=1.5116$ and of the formula

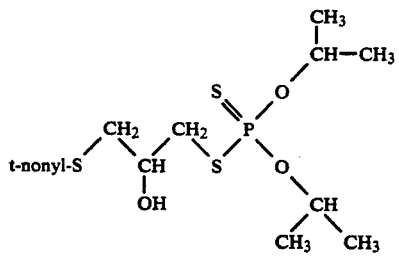

44.3 g of this product are then initially introduced into 10 ml of toluene, and 28.7 g of iso-dodecenylsuccinic anhydride are added dropwise. The mixture is kept at 50° C. for 3 hours, while stirring constantly; 0.1 g of 4-toluenesulfonic acid is then added and the mixture is kept at 50° C. for a further 3 hours, while stirring. It is then cooled and washed with water, and the organic phase is dried over sodium sulfate and freed from the solvent by application of reduced pressure. 71.7 g (100.0% of theory) of a mixture of the two compounds

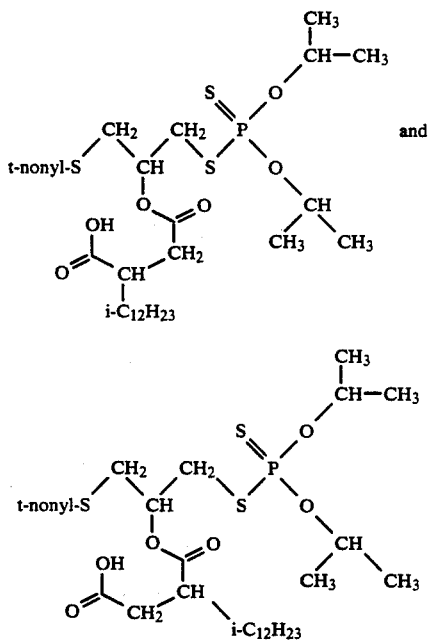

which are isomeric in respect of the position of the iso-dodecenyl group, remain as a virtually colourless viscous liquid having the refractive index $n_D^{20} = 1.5003$ and IR absorption maxima at wave numbers of 1709 cm$^{-1}$ and 1741 cm$^{-1}$.

EXAMPLE 2

The same compounds as in Example 1 can also be obtained by the following synthesis variant;

88.6 g of tert-nonyl 2,3-epoxypropyl thioether are added dropwise to 88.0 g of O,O'-diisopropyldithiophosphoric acid in 100 ml of toluene in the course of about 30 minutes, during which the reaction mixture heats up. The reaction temperature is then kept at 70° C. for 3 hours, the mixture is cooled, 12 ml of a 5% hydrogen peroxide solution are added, the mixture is heated at 50° C. for 10 minutes, the aqueous phase is separated off, the organic phase is washed successively with 30 ml of saturated sodium bicarbonate solution and twice with 50 ml of water each time and dried with sodium sulfate, and the solvent is removed by application of reduced pressure. 166.2 g (94% of theory) of the intermediate from Example 1 remain as a viscous colourless liquid having the refractive index $n_D^{20} = 1.5132$.

160 g of this product are then initially introduced into 100 ml of toluene and 10 ml of dibutyl ether, and 0.2 g of 4-toluenesulfonic acid is added. 104 g of iso-dodecenylsuccinic anhydride are then added dropwise. The mixture is kept at 70° C. for 5 hours, while stirring constantly, and is then cooled, washed once with 50 ml of water and, after drying over sodium sulfate, is freed from the solvent by application of reduced pressure 244.2 g (94% of theory) of the end product obtained according to Example 1 remain as a viscous pale yellow liquid with $n_D^{20} = 1.5001$.

EXAMPLE 3

27.6 g of O,O'-diisobutyldithiophosphoric acid are reacted with 26.0 g of tert-nonyl 2,3-epoxypropyl thioether as described in Example 1. 51.8 g (98.7% of theory) of an intermediate are obtained as a colourless liquid having the refractive index $n_D^{20} = 1.5062$ and the formula 24.5 g of iso-dodecenylsuccinic anhydride are added to 40.2 g of this product as described in Example 1. 62.9 g (98.9% of theory) of a mixture of the two compounds 1.5116 and of the formula

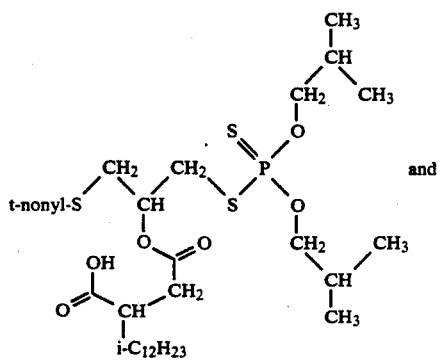

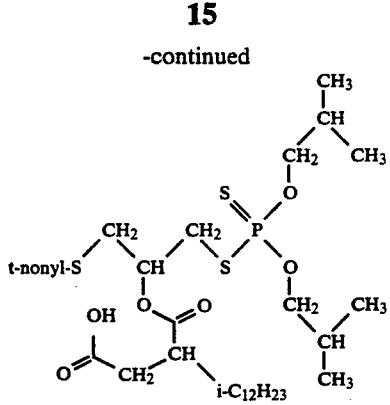

which are isomeric in respect of the position of the iso-dodecenyl group are obtained as a viscous pale yellow liquid having the refractive index $n_D^{20}=1.4942$.

EXAMPLE 4

30.0 g of O,O'-di-n-pentyl-dithiophosphoric acid are reacted with 25.2 g of tert-nonyl 2,3-epoxypropyl thioether at 60° C. as described in Example 1. 53.9 g (99% of theory) of an intermediate are obtained as a colourless liquid of the formula

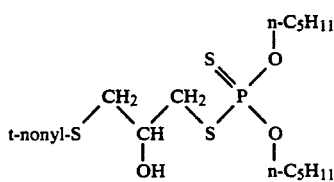

with $n_D^{20}=1.5051$ and a chemical shift in the $^{31}$P-NMR of $\delta=96$ ppm.

26.3 g of iso-dodecenylsuccinic anhydride are added dropwise to 45.7 g of this product, during which the temperature rises. After addition of 0.1 g of 4-toluene-sulfonic acid, the reaction mixture is kept at 50° C. for 3 hours, cooled, and worked up as described in Example 1. 66.2 g (93% of theory) of a mixture of the isomers

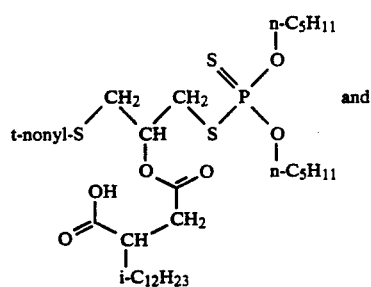

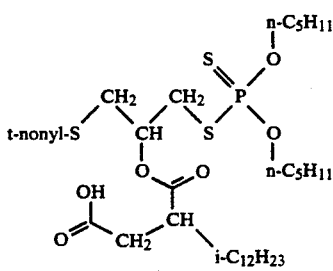

are obtained as a pale yellow liquid having the refractive index $n_D^{20}=1.4984$ and a chemical shift in the $^{31}$P-NMR of $\delta=96$ ppm.

EXAMPLE 5

32 g of O,O'-di(2-ethylhexyl)dithiophosphoric acid are reacted with 20.5 g of tert-nonyl 2,3-epoxypropyl thioether as described in Example 1. 49.2 g (95.5% of theory) of an intermediate are obtained as a colourless liquid having the refractive index $n_D^{20}=1.4919$ and the formula

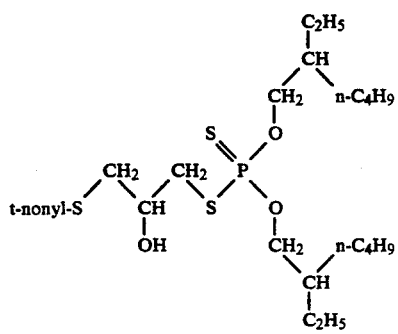

38.7 g of this product are reacted with 19.0 g of iso-dodecenylsuccinic anhydride analogously to Example 1. 56.8 g (100% of theory) of a mixture of the isomers

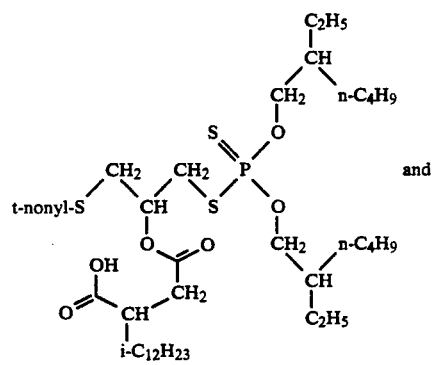

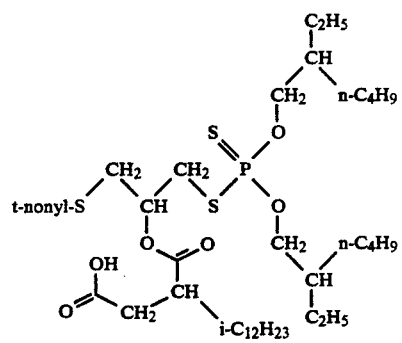

are obtained as a viscous pale yellow liquid having the refractive index $n_D^{20}=1.4907$.

EXAMPLE 6

50.0 g of tert-dodecyl 2,3-epoxypropyl thioether are added dropwise while stirring to 39.4 g of O,O'-diisopropyl-dithiophosphoric acid under nitrogen and while cooling with a waterbath, during which the temperature does not rise above 20° C. The mixture is then heated at 40° C. for 1 hour, and volatile constituents are subsequently stripped off in vacuo. 87.8 g of an intermediate remain as a viscous colourless liquid having the refractive index $n_D^{20}=1.5093$, a chemical shift in the $^{31}$P-NMR (CDCl$_3$) of $\delta=92.6$ ppm and the formula

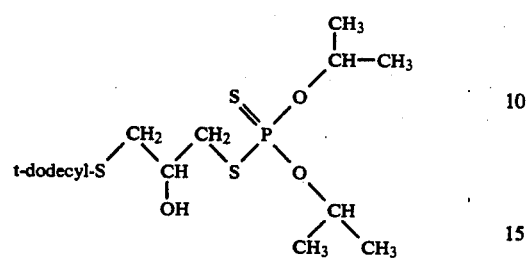

32.5 g of this product are then initially introduced into 10 ml of toluene, 0.1 g of 4-dimethylaminopyridine is added, and 19.2 g of iso-dodecenylsuccinic anhydride are added dropwise. The mixture is kept at 50° C. for 7 hours while stirring constantly. It is then cooled, diluted with toluene and washed with water, and the organic phase is dried over sodium sulfate and freed from the solvent by application of a reduced pressure. 51 g (100% of theory) of a mixture of the isomers

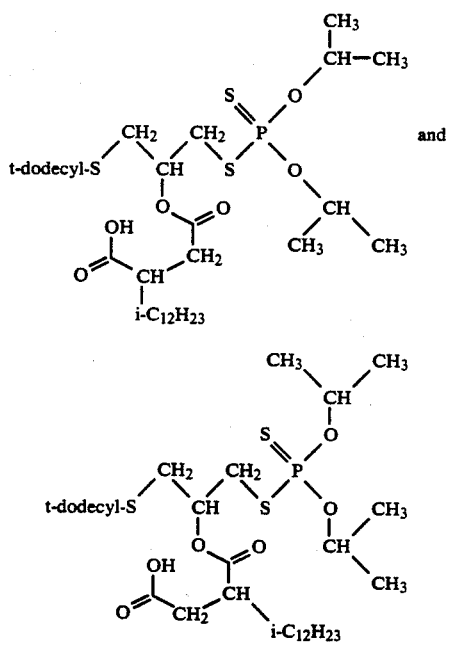

remain as a viscous pale yellow liquid having the refractive index $n_D^{20}=1.4997$ and IR absorption maxima at the wave numbers 1709 cm$^{-1}$ and 1741 cm$^{-1}$ (KBr).

EXAMPLE 7

21.7 g of tert-nonyl 2,3-epoxypropyl thioether are added dropwise to 46.7 g of O,O'-di-n-dodecyl-dithiophosphoric acid in 50 ml of dibutyl ether under nitrogen and while cooling with a waterbath, during which the temperature does not rise above 20° C. The mixture is then heated at 60° C. for 2 hours. After addition of 0.1 g of 4-toluenesulfonic acid, 26.6 g of iso-dodecenylsuccinic anhydride are added to the reaction mixture. The mixture is kept at 60° C. for 6 hours, while stirring constantly. It is then cooled, diluted with toluene and washed with water, and the organic phase is dried over sodium sulfate and freed from the solvent by application of reduced pressure. 80.4 g (84% of theory) of a mixture of the isomers

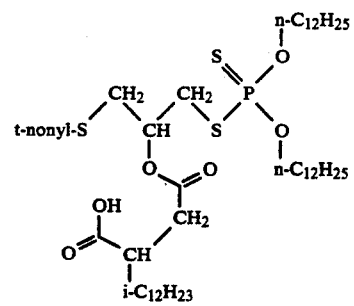

and

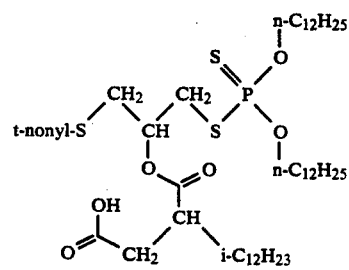

remain as a viscous pale yellow liquid having the refractive index $n_D^{20}=1.4865$ and IR absorption maxima at the wave numbers 1710 cm$^{-1}$ and 1738 cm$^{-1}$ (KBr).

EXAMPLE 8

25.5 g of tert-nonyl 2,3-epoxypropyl thioether are added dropwise to 55.0 g of O,O'-didodecyl-dithiophosphoric acid in 50 ml of dibutyl ether under nitrogen and while cooling with a waterbath, during which the temperature does not rise above 20°-25° C. The mixture is then heated at 60° C. for 2 hours. After cooling to room temperature and addition of 0.1 g of 4-toluenesulfonic acid and 18.0 g of tetrahydrophthalic anhydride, the reaction mixture is kept at 60° C. for 5 hours, while stirring constantly. A further 3.6 g (20% excess) of tetrahydrophthalic anhydride is then added and the mixture is heated under reflux for 5 hours. It is then cooled, the insoluble residue is filtered off, the filtrate is diluted with toluene and washed with water, and the organic phase is dried over sodium sulfate and freed from the solvent by application of reduced pressure. 94.0 g (95% of theory) of the compound

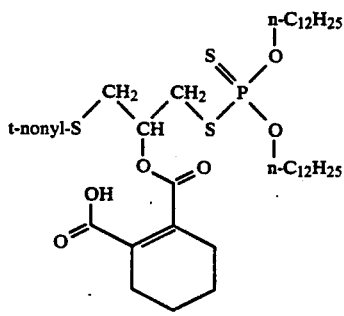

remain as a pale yellow liquid having the refractive index $n_D^{20}=1.4930$. After a few days, a further 5 g of precipitate are filtered off. The liquid now has a refractive index of $n_D^{20} = 1.4936$ and IR absorption maxima at the wave numbers 1709 cm$^{-1}$ (KBr).

EXAMPLE 9

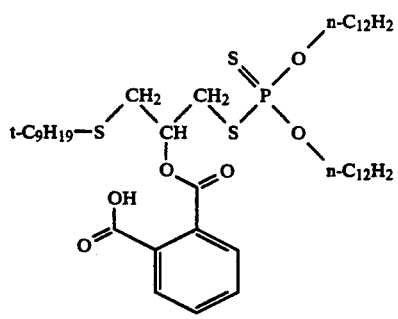

a) 31.6 g of tert-nonyl 2,3-epoxypropyl thioether are reacted with 80.0 g of 85% strength O,O'-didodecyl-dithiophosphoric acid analogously to Example 1a. 88.9 g (75% of theory) of a colourless liquid with $n_D^{20} = 1.4924$ are obtained.

b) 36.0 g of the product described above and 9.2 g of phthalic anhydride are dissolved in 30 ml of dibutyl ether. After addition 0.1 g of 4-dimethylaminopyridine, 8.0 g of diethylamine are added dropwise. After the mixture has been stirred at 70° C. for 8 hours, it is cooled, acidified with 2N hydrochloric acid, diluted with toluene and extracted. The organic phase which has been separated off is washed twice with 50 ml of water, dried over sodium sulfate and concentrated in vacuo. 41.6 g (95% of theory) of a yellow liquid with $n_D^{20} = 1.5071$ are obtained. IR (P=S) 1731 cm$^{-1}$

EXAMPLE 10

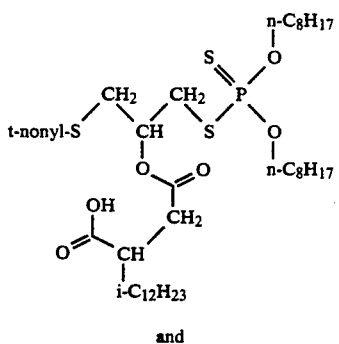

and

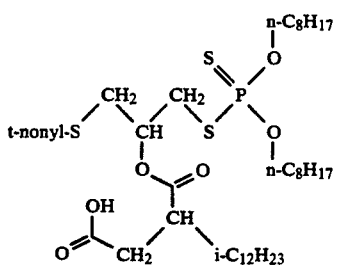

153.3 g (0.50 mol) of di-n-octyl phosphite and 16.0 g (0.5 mol) of sulfur are stirred at 50° C. under a nitrogen atmosphere, and ammonia gas is passed in until the uptake of gas has ended. During this procedure, the reaction temperature is kept at 20° to 25° C. After the mixture has been stirred at this temperature for a further 90 minutes, nitrogen is passed through the solution for 30 minutes to remove the excess ammonia. After addition of 5 g of active charcoal, the mixture is filtered and the filtrate is freed from the solvent in vacuo. 172.8 g (97% of theory) of a pale grey waxy mass remains:

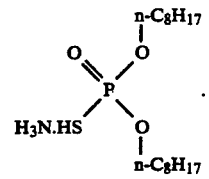

118.6 g of this product are dissolved in 400 ml of toluene and the solution is washed successively with 100 ml of 5N hydrochloric acid and three portions of 100 ml of water. The organic phase is concentrated in vacuo, and 110.1 g of a pale yellow liquid remain:

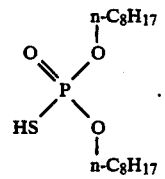

25.96 g of 2,3-epoxypropyl tert-nonyl thioether are added dropwise to a solution of 40.62 g of the O,O-di-n-octyl-monothiophosphoric acid obtained above in 200 ml of toluene under nitrogen. When the addition has ended, the mixture is heated at 60° C. for 2 hours and the solvent is then distilled off in vacuo. 62.45 g of a pale yellow oil which, according to $^{31}$P-NMR (CDCl$_3$) consists to the extent of about 80% of the desired product ($\delta$29.8 ppm) and to the extent of 20% of the isomeric compound (O-n-Octyl)$_2$P(=S)—O—CH$_2$CH(OH)CH$_2$—$^t$C$_9$H$_{19}$, remain:

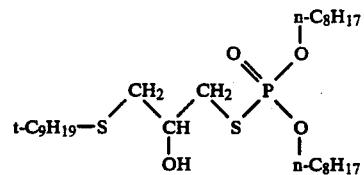

49.5 g of this product are dissolved in 50 ml of toluene. After addition of 0.5 g of methanesulfonic acid, 22.6 g (85 mmol) of iso-dodecenylsuccinic anhydride are added dropwise, and the mixture is heated at 70° for 22 hours. After cooling, the mixture is washed with 75 ml each of water and 5% sodium sulfate solution. After the solvent has been distilled off, 66 g of a pale yellow viscous oil remain. 6.0 g of the crude product are purified by column chromatography (chloroform/silica gel). 3.6 g (60%) of the isomer mixture are obtained as the main fraction. $^{31}$P-NMR: only one resonance signal at $\delta = 29.1$ ppm.

EXAMPLE 11

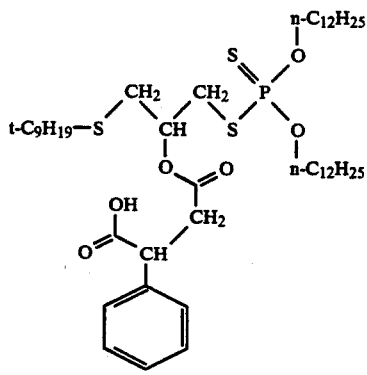

and

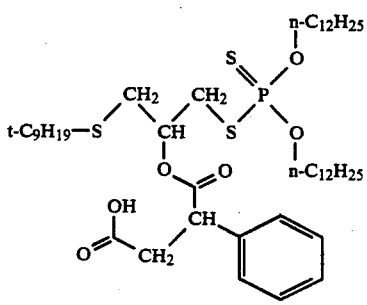

The intermediate is prepared analogously to Example 8 from 28.0 g of O,O-didodecyl-dithiophosphoric acid and 13.0 g of tert-nonyl 2,3-epoxypropyl thioether in 50 ml of dibutyl ether. A total of 16.9 g of phenylsuccinic anhydride and 3.4 g of triethylamine are then added, and the mixture is heated to about 100° C. until the anhydride has melted and, after addition of 20 ml of tetrahydrofuran, is stirred at about 25° C. for 48 hours. It is then washed with 50 ml of 2N hydrochloric acid and 2×50 ml of water and dried over sodium sulfate, and the solvent is distilled off in vacuo. Chromatography (methylene chloride/diethyl ether/petroleum ether 1:4:5) gives 3.4 g of the product with $n_D^{20}=1.5037$, IR 1712, 1742 (film on KBr) from a 10 g sample.

EXAMPLE 12

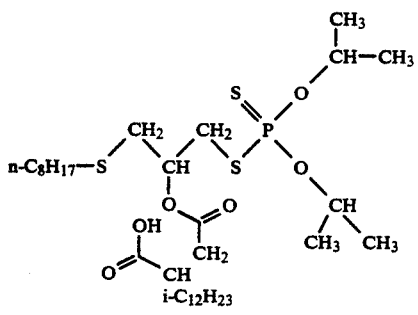

and

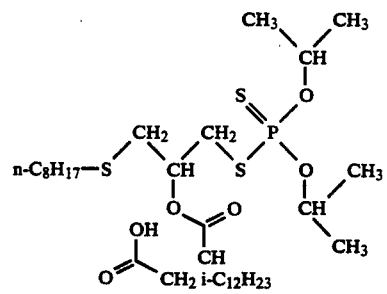

17.14 g of O,O-diisopropyldithiophosphoric acid are reacted with 16.19 g of n-octyl 2,3-epoxypropyl thioether analogously to Example 1. 32.6 g (80%) of the intermediate

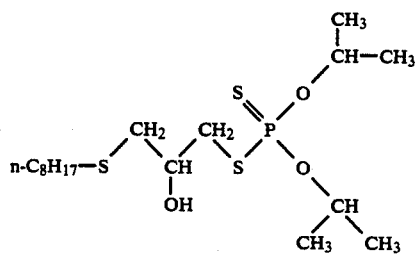

are obtained.

20.83 g of this product are heated at 80° C. in 30 ml of toluene with 12.65 g of isododecylsuccinic anhydride for 8 hours. To bring the reaction to completion, 30 ml of dibutyl ether and 3.0 g of diazabicyclooctane are then added and the mixture is stirred at 25° C. for 48 hours. It is then diluted with toluene, washed successively with dilute hydrochloric acid, 2×water and sodium sulfate solution and dried over sodium sulfate, and the solvent is distilled off in vacuo. 31.5 g (94% of theory) of a pale yellow viscous liquid remain.

IR 1711, 1740 cm$^{-1}$.

EXAMPLE 13

20.6 g of tert-dodecyl 2,3-epoxypropyl thioether are added dropwise to 20.6 g of O,O'-di-(2-ethylhexyl)-dithiophosphoric acid in 100 ml of toluene, while stirring constantly. The mixture is then heated at 60° C. for 5 hours. After addition of 6.7 g of methylsuccinic anhydride, 80 ml of dibutyl ether and 0.2 g of 4-toluenesulfonic acid, the reaction mixture is kept at 120° C. for 5 hours. It is then cooled and washed with 100 ml of water and, after drying over sodium sulfate, the organic phase is freed from the solvent by application of reduced pressure. 38.0 g (90% of theory) of a mixture of the compounds

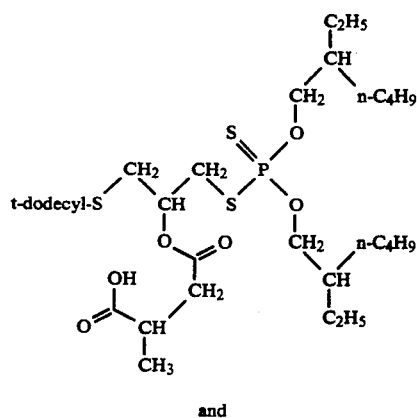

and

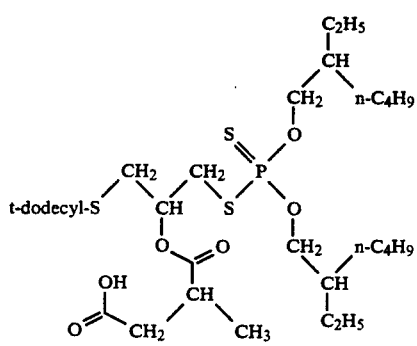

are obtained as a viscous pale yellow liquid having the refractive index $n_D^{20}=1.4914$ and IR absorption maxima at the wave numbers 1712 cm$^{-1}$ and 1741 cm$^{-1}$.

The compounds listed in Table 1 are obtained analogously to the examples described by using the corresponding starting compounds.

EXAMPLE 20

18.7 g of tert-nonyl 2,3-epoxypropyl thioether are added dropwise to 20.9 g of O,O'-diisobutyl-dithiophosphoric acid in 20 ml of toluene under nitrogen and while cooling with a waterbath, during which the temperature does not rise above 20°–25° C. The mixture is then heated at 60° C. for 2 hours. After addition of 30.4 g of n-octadecylsuccinic anhydride, the reaction mixture is kept at 110° C. for 3 hours. It is then cooled, diluted with toluene and washed with water, and the organic phase is dried over sodium sulfate and freed from the solvent by application of reduced pressure.

TABLE 1

Examples 14–19; compounds of the formula

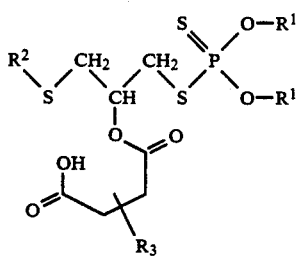

| Example No. | R$^1$ | R$^2$ | R$^3$ | Yield in % of theory | Procedure as Example | Physical data |
|---|---|---|---|---|---|---|
| 14 | —CH(CH$_3$)$_2$ | tert-C$_9$H$_{19}$ | —CH$_2$CH=CH—C$_9$H$_{19}$ | 95 | 1 | colourless, viscous $n_D^{20} = 1.4961$ IR max.: 1710 and 1741 cm$^{-1}$ |
| 15 | —CH$_2$CH(CH$_3$)$_2$ | tert-C$_9$H$_{19}$ | —CH$_2$CH=CH—C$_9$H$_{19}$ | 93 | 3 | colourless, viscous $n_D^{20} = 1.4948$ IR max.: 1711 and 1741 cm$^{-1}$ |
| 16 | —CH(CH$_3$)$_2$ | tert-C$_{12}$H$_{25}$ | —CH$_2$CH=CH—C$_5$H$_{11}$ | 94 | 6, but 16 h at 50° C. | colourless, viscous $n_D^{20} = 1.5010$ IR max.: 1711 and 1741 cm$^{-1}$ |
| 17 | —CH(CH$_3$)$_2$ | tert-C$_9$H$_{19}$ | —CH$_2$CH=CH—C$_5$H$_{11}$ | 92 | 1 | colourless, viscous $n_D^{20} = 1.4980$ IR max.: 1711 and 1740 cm$^{-1}$ |

TABLE 1-continued

Examples 14-19; compounds of the formula

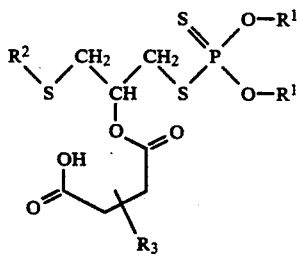

| Example No. | R¹ | R² | R³ | Yield in % of theory | Procedure as Example | Physical data |
|---|---|---|---|---|---|---|
| 18 | —CH(CH₃)CH₃ | tert-C₉H₁₉ | n-C₁₈H₃₇ | 83 | 1, but 16 h at 50° C. | pale yellow wax, melting point 53-59° C. IR max.: 1709 and 1741 cm⁻¹ |
| 19 | —CH₂CH(n-C₄H₉)C₂H₅ | tert-C₁₂H₂₅ | —CH₂CH=CH—C₅H₁₁ | 83 | 1, but 16 h at 50° C. | colourless, viscous $n_D^{20}$ = 1.4940 IR max.: 1711 and 1741 cm⁻¹ |

63.0 g (89% of theory) of a mixture of the compounds

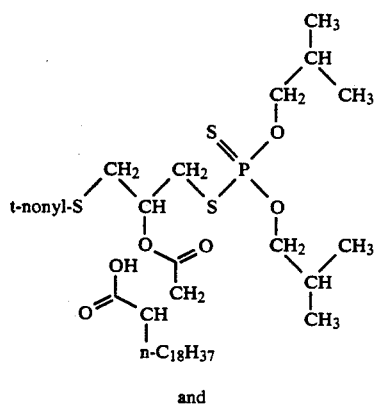

and

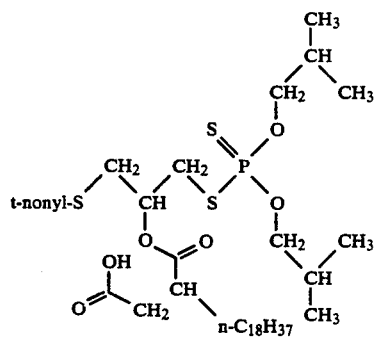

remain as a pale yellow, slowly solidifying wax having the melting range 47°-56° C. and IR absorption maxima at the wavenumbers 1710 cm⁻¹ and 1741 cm⁻¹ (KBr).

EXAMPLE 21

80.0 g of 85% strength O,O'-di-dodecyldithiophosphoric acid are reacted with 31.6 g of tert-nonyl 2,3-epoxypropyl thioether analogously to Example 1. 88.9 g (75% of theory) of an intermediate are obtained as a colourless liquid having the refractive index $n_D^{20}$=1.4924 and the formula

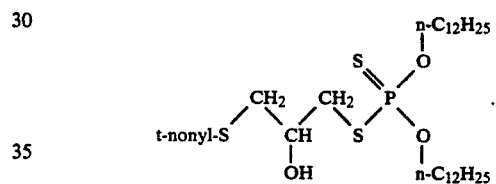

0.1 g of dimethylaminopyridine is then first added to a solution of 36.0 g of this product and 9.2 g of phthalic anhydride in 30 ml of dibutyl ether, and 8.0 g of triethylamine are subsequently added dropwise. The mixture is stirred at 70° C. for 8 hours. It is then cooled and acidified with 2 molar hydrochloric acid, and after dilution with toluene, the organic phase is separated off. This is washed twice with 50 ml of water, dried over sodium sulfate and concentrated in vacuo. 41.6 g (75% of theory) of the compound

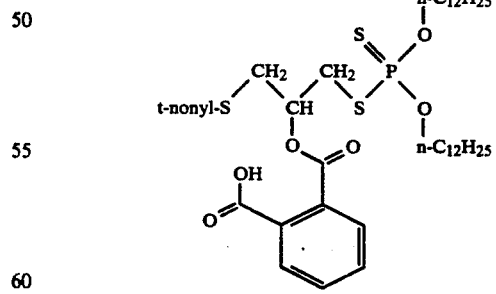

are obtained as a yellow liquid having the refractive index $n_D^{20}$=1.5071 and an IR absorption maximum at 1731 cm⁻¹.

The compounds listed in Table 2 are obtained by the preparation process described in Example 21 using the corresponding starting compounds. Where stated, working up is carried out by flash chromatography on silica gel using a gradiant of methylene chloride/acetone.

EXAMPLE 26

Diisotridecylammonium salt of the compound from Example 1

8.21 g of industrial ditridecylamine are added dropwise to 15.0 g of the product from Example 1 in 20 ml of toluene. After thorough mixing, the solvent is distilled off by application of reduced pressure. 21.7 g (93% of theory) of a mixture of the isomeric compounds -continued

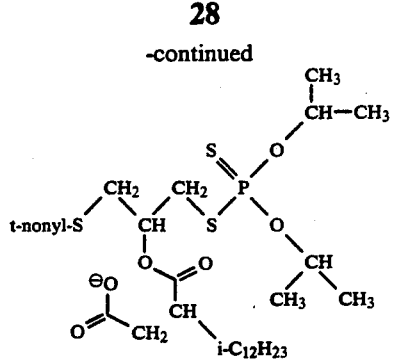

TABLE 2

Examples 22-25; compounds of the formula

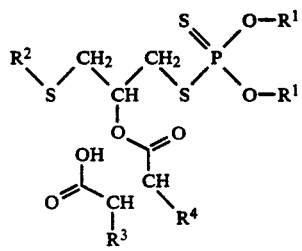

| Example No. | $R^1$ | $R^2$ | $R^3, R^4$ | Yield in % of theory | Procedure as Example | Physical data |
|---|---|---|---|---|---|---|
| 22 | n-$C_{12}H_{25}$ | tert-$C_9H_{19}$ | $R^3 + R^4 = $ ⌬ | 50 | 21, flash chromatography | yellow, viscous $n_D^{20} = 1.5026$ |
| 23 | —$CH_2$—CH—n-$C_4H_9$ / $C_2H_5$ | tert-$C_{12}H_{25}$ | H, H | 50 | 21, flash chromatography | colourless, viscous; $n_D^{20} = 1.4971$ 1H-NMR (200 MHz, $CDCl_3$) δ = 2.65 ppm |
| 24 | n-$C_{12}H_{25}$ | tert-$C_9H_{19}$ | Isomer mixture with $R^3$ = n-$C_6H_{13}$, $R^4$ = H and $R^3$ = H, $R^4$ = n-$C_6H_{13}$ | 90 | 21 | colourless, viscous $n_D^{20} = 1.4840$ IR max.: 1710 and 1742 $cm^{-1}$ |
| 25 | —$CH_2$—$CH(CH_3)_2$ | tert-$C_9H_{19}$ | $R_3$ = —$CH_2$—CH=CH—$(CH_2)_4C$-$H_3$ $R_4$ = H | 95% | 9 | colourless viscous liquid $n_D^{20} = 1.4900$ IR- 1710; 1740 $cm^{-1}$ |

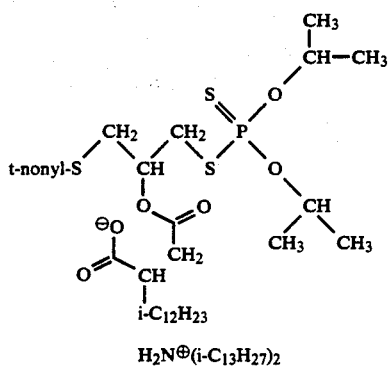

and remain as a viscous yellow liquid having the refractive index $n_D^{20} = 1.4905$.

EXAMPLE 27

Lithium Salt of the Compound from Example 3

15.0 g of the product from Example 3 are dissolved in 100 ml of toluene. After addition of 0.90 g of lithium hydroxide, the mixture is heated under reflux and under nitrogen, using a water separator, until no further water of reaction passes over. The solvent is then distilled off under reduced pressure. 15.7 g of the isomer mixture corresponding to the formulae

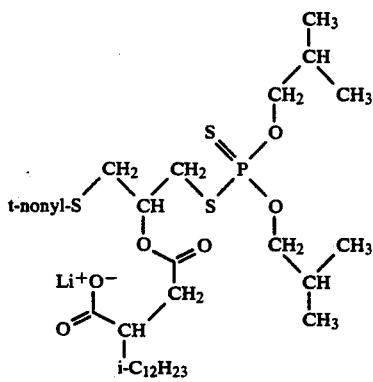

and

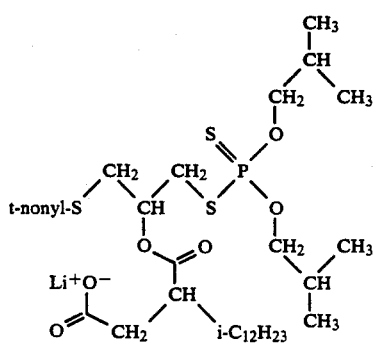

are obtained as a viscous yellow liquid having the refractive index $n_D^{20} = 1.5060$;

| Microanalysis: | C | H | S | P | Li |
|---|---|---|---|---|---|
| Calculated | 59.2% | 9.37% | 13.2% | 4.23% | 0.95% |
| Found | 60.5% | 9.13% | 12.2% | 4.02% | 0.93% |

Use Examples

EXAMPLES 28–44

Wear Prevention and Corrosiveness with Respect to Copper

ASTM standard method D-2783-81 using the Shell four ball tester (FBT) is used for testing for suitability as an antiwear additive. An oil having a viscosity of 26.2 mm²/s at 40° C. and 4.8 mm²/s at 100° C. and a sulfur content of 0.54% is used as the base oil. The compound to be tested from the particular example mentioned is added to the base oil in each case in an amount of 1% by weight. The following are determined:

a) The weld load WL as the load (in kg) at which the 4 balls weld together within 10 s, and b) the average wear scar diameter WSD under a load of 20 kg over a period of one hour (in mm).

The corrosiveness with respect to copper is determined in accordance with ASTM standard method D-130. For this, a polished strip of copper is immersed for three hours in a sample composition kept at 120° C. This consists of the base oil described above with additionally 0.03% of a commercially available copper passivator of the 1-di-(2-ethylhexyl)-aminomethyltolutriazole type and, with the exception of a comparison sample, in each case 1% of the compound according to the invention. The copper strip is then removed from the oil, cleaned and evaluated, the ASTM Copper Strip Corrosion Standards being used for the evaluation. The evaluation comprises four stages:

1—no deposit
2—moderate deposite
3—severe deposit
4—corrosion, a fine subclassification also be being made within the numerical groups 1 to 4 on the basis of shadowing on the samples. In the qualitative evaluation from A to E, the rating A precedes B, B precedes C and so on.

The results on 1% strength solutions of the particular compounds according to the invention in the base oil described above are shown in Table 3.

TABLE 3

| Example No. | Compound from Example No. | Wear protection (FBT) | | Corrosiveness ASTM D 130 |
|---|---|---|---|---|
| | | WL/kg | WSD/mm | |
| 28 | 1 | 160 | 0.35 | 2A |
| 29 | 3 | 160 | 0.39 | 1B |
| 30 | 4 | 160 | 0.37 | 1B |
| 31 | 5 | 160 | 0.39 | 1B |
| 32 | 6 | 140 | 0.38 | 2A |
| 33 | 14 | 150 | 0.32 | 2A |
| 34 | 20 | 140 | 0.28 | 1B |
| 35 | 15 | 150 | 0.30 | 1B |
| 36 | 17 | 140 | 0.34 | 1B |
| 37 | 18 | 150 | 0.29 | 1B |
| 38 | 19 | 150 | 0.31 | 1B |
| 39 | 13 | 160 | 0.35 | 1B |
| 40 | 21 | 140 | 0.40 | 1B |
| 41 | 22 | 140 | 0.37 | 1B |
| 42 | 23 | 150 | 0.35 | 1B |
| 43 | 24 | 140 | 0.38 | 1B |
| 44 | 25 | 140 | 0.40 | 1B |
| no active compound | | 130 | 0.82 | 3B |

EXAMPLES 45–53

Rust-Preventing Properties

Products according to the invention are tested in accordance with ASTM standard method D 665 B in respect of the rust-preventing properties in turbine oils in the presence of water.

The test method is designed such that 300 ml of the oil to be tested of ISO VG class VG 46, comprising 0.25% of the compound according to the invention, and 30 ml of simulated sea-water according to ASTM D 665 B are stirred in a vessel at 60° C. for 24 hours. A cylindrical steel specimen is immersed in the oil to be tested. The degree of corrosion of the steel specimen is measured, 0 meaning no rust formation and 3 severe rust formation. The numbers 1 and 2 accordingly indicate degrees of corrosion between these two extreme values. The results of the test are summarized in Table 4.

TABLE 4

Results of ASTM test D 665 B for rust-preventing properties

| Example No. | Compound from Example No. | Evaluation |
|---|---|---|
| 45 | 1 | 0 |
| 46 | 3 | 0 |
| 47 | 17 | 0 |
| 48 | 13 | 0 |
| 49 | 21 | 0 |
| 50 | 22 | 0 |
| 51 | 23 | 0 |
| 52 | 24 | 0 |
| 53 | 25 | 0 |
| Comparison without an active | | 3 |

TABLE 4-continued

Results of ASTM test D 665 B for rust-preventing properties

| Example No. | Compound from Example No. | Evaluation |
|---|---|---| compound according to the invention

What is claimed is:

1. A compound of the formula (I)

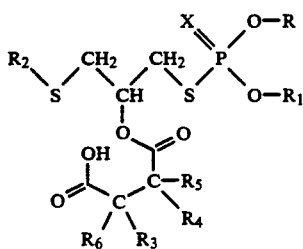

in which X is oxygen or sulfur, R and $R_1$ independently of one another are $C_3$-$C_{30}$alkyl, $R_2$ is $C_4$-$C_{18}$alkyl; $R_3$, $R_4$, $R_5$ and $R_6$ independently of one another are H, $C_1$-$C_{20}$alkyl, $C_3$-$C_{20}$alkenyl, benzyl, phenyl or phenyl which is substituted by $C_1$-$C_{12}$alkyl or $R_5$ and $R_6$ are a direct bond, and $R_3$ and $R_4$ are as defined above; or $R_3$ and $R_4$ together are trimethylene, tetramethylene,

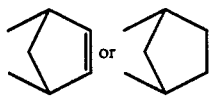

and $R_5$ and $R_6$ are a direct bond or H; or $R_3$ and $R_6$ together are a group =$CH_2$ and $R_4$ and $R_5$ and $R_5$ are H; or $R_4$ and $R_5$ together are a group =$CH_2$ and $R_3$ and $R_6$ are H; or $R_3$, $R_4$, $R_5$ and $R_6$ together are

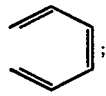

or a salt thereof.

2. A compound according to claim 2, in which R and $R_1$ independently of one another are $C_3$-$C_{18}$alkyl and $R_2$ is $C_4$-$C_{18}$alkyl; one of the substituents $R_3$ or $R_4$ is H, $C_1$-$C_{20}$alkyl or $C_3$-$C_{20}$alkenyl and the other is hydrogen; or $R_3$ and $R_4$ together are trimethylene, tetramethylene,

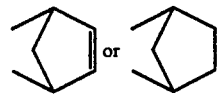

and $R_5$ and $R_6$ are hydrogen or a direct bond; or $R_3$, $R_4$, $R_5$ and $R_6$ together are

3. A compound according to claim 2, in which X is sulfur, R and $R_1$ independently of one another are $C_3$-$C_{12}$alkyl; $R_2$ is $C_4$-$C_{12}$alkyl; one of the substituents $R_3$ or $R_4$ is $C_1$-$C_{20}$alkyl or $C_4$-$C_{20}$alkenyl and the other is hydrogen; or $R_3$ and $R_4$ together are trimethylene or tetramethylene; and $R_5$ and $R_6$ are hydrogen or a direct bond.

4. A compound according to claim 3, in which R and $R_1$ are in each case identical and are isopropyl or 2-methylpropyl, $R_2$ is tert-nonyl or tert-dodecyl, one of the substituents $R_3$ or $R_4$ is $C_8$-$C_{12}$alkyl or -alkenyl and the other is hydrogen, and $R_5$ and $R_6$ are hydrogen.

5. A compound according to claim 1, in which R and $R_1$ are identical.

6. A compound according to claim 1, in which X is sulfur.

7. A compound of the formula (I) or a salt thereof according to claim 1, in which the salt is an alkali metal, alkaline earth metal, zinc or copper salt or an ammonium or mono-, di- or tri-$C_1$-$C_{18}$alkyl-substituted ammonium salt, or mixtures thereof.

8. A compound according to claim 7, in which the salt is an alkali metal salt or a mono- or di-$C_8$-$C_{18}$alkyl-substituted ammonium salt.

9. A composition comprising a) a lubricant or a hydraulic or metalworking fluid and b) at least one compound of the formula (I) according to claim 1.

10. A composition according to claim 9, comprising 0.01 to 5% by weight of at least one compound of the formula (I).

11. A composition according to claim 9, in which component a) is a lubricant.

12. A composition according to claim 9, which additionally comprises one or more other additives selected from the group consisting of anticorrosion agents, rust inhibitors, metal deactivators, agents for improving the viscosity index, dispersing agents, antioxidants, pour-point depressants and high pressure and antiwear additives.

13. A method for improving the useful properties of a composition comprising a major amount of a lubricant, a hydraulic fluid or a metalworking fluid which method comprises adding to said composition a minor property improving amount of at least one compound of formula (I) according to claim 1.

* * * * *